(12) United States Patent
Gerardi (10) Patent No.: US 11,412,775 B2
(45) Date of Patent: Aug. 16, 2022

(54) TOBACCO-DERIVED COMPOSITION

(71) Applicant: R.J. REYNOLDS TOBACCO COMPANY, Winston-Salem, NC (US)

(72) Inventor: Anthony Richard Gerardi, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 3008 days.

(21) Appl. No.: 13/647,670

(22) Filed: Oct. 9, 2012

(65) Prior Publication Data

US 2014/0096780 A1     Apr. 10, 2014

(51) Int. Cl.
*A24B 15/26* (2006.01)
*A24B 15/30* (2006.01)

(52) U.S. Cl.
CPC ............ *A24B 15/26* (2013.01); *A24B 15/303* (2013.01)

(58) Field of Classification Search
None
See application file for complete search history.

(56) References Cited

U.S. PATENT DOCUMENTS

| | | |
|---|---|---|
| 5,065,775 A | 11/1991 | Fagg |
| 5,311,886 A * | 5/1994 | De Grandpre ......... A24B 15/24 131/297 |
| 5,565,435 A | 10/1996 | Yoneyama et al. |
| 2005/0042311 A1 | 2/2005 | Lee et al. |
| 2011/0174323 A1 | 7/2011 | Coleman, III et al. |
| 2011/0259353 A1 | 10/2011 | Coleman, III et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. et al. |

FOREIGN PATENT DOCUMENTS

| | | |
|---|---|---|
| CN | 101735191 | 6/2010 |
| CN | 102090712 | 6/2011 |
| WO | WO 03053179 | 7/2003 |

OTHER PUBLICATIONS

Murphy, JOC, Nov. 1960, 25, 2063-2064.*
Arrangement and Classification of Tobacco Types, Nov. 2006, pp. 18, 129.*
Watanabe et al., Flavonoid and Certain Related Phenolic Compounds in Parts of the Tobacco Flower, Archieves of Biochemistry and Biophysics 112, 114 (Year: 1965).*
Fathiazad et al., "Extraction of Flavonoids and Quantification of Rutin From Waste Tobacco Leaves," *Iranian Journal of Pharmaceutical Research*, 2006, 3: pp. 222-227.

(Continued)

*Primary Examiner* — Phu H Nguyen
(74) *Attorney, Agent, or Firm* — Womble Bond Dickinson (US) LLP (57) ABSTRACT

Isolated O-methylated flavonoid compounds and mixtures of o-methylated flavonoid compounds derived from a plant of the *Nicotiana* species and methods of obtaining such compounds are provided. The o-methylated flavonoids can be combined with tobacco materials to produce tobacco products (e.g., smoking articles) to enhance the sensory characteristics thereof. The o-methyl flavonoids can alternatively be combined with non-tobacco materials for dietary supplement and/or pharmaceutical use.

18 Claims, 2 Drawing Sheets

(56) References Cited

OTHER PUBLICATIONS

Forkmann et al., "Metabolic Engineering and Applications of Flavonoids," *Current Opinion in Biotechnology*, 2001, vol. 12, pp. 155-160.
Kaushik et al., "Preliminary Phytochemical Screening and HPTLC Fingerprinting of *Nicotiana tabacum* Leaf," *Journal of Pharmacy Research*, 2010, 3 (5), pp. 1144-1145.
Roda et al., "Allometric Analysis of the Induced Flavonols on the Leaf Surface of Wild Tobacco (*Nicotiana attenuata*)," *Phytochemistry*, 2003, 62: pp. 527-536.
Rodgman, et al., "The Chemical Components of Tobacco and Tobacco Smoke," *CRC Press*, 2009, p. 524.
Watanabe et al., "Flavonoid and Certain Related Phenolic Compounds in Parts of the Tobacco Flower," *Archives of Biochemistry and Biophysics*, 1965, vol. 112, Issue 1, pp. 111-114 (Abstract).
Wen et al., "Methylated Flavonoids Have Greatly Improved Intestinal Absorption and Metabolic Stability," *Drug Metabolism and Disposition*, 2006, vol. 34, No. 10, pp. 1786-1792.
Wollenweber et al., "Chemodiversity of Surface Flavonoids in Solanaceae," *Z. Naturforsch*, 2005, 60c: pp. 661-670.
Yang et al., "Methyl Ethers of Quercetin in Tobacco Flowers," *The Journal of Organic Chemistry*, 1960, pp. 2063-2064, vol. 25.

\* cited by examiner

TOBACCO-DERIVED COMPOSITION

FIELD OF THE INVENTION

The present invention relates to products made or derived from tobacco, or that otherwise incorporate tobacco or components of tobacco, and are intended for human consumption. Of particular interest are ingredients or components obtained or derived from plants or portions of plants from the *Nicotiana* species.

BACKGROUND OF THE INVENTION

Cigarettes, cigars, and pipes are popular smoking articles that employ tobacco in various forms. Such smoking articles are employed by heating or burning tobacco to generate aerosol (e.g., smoke) that may be inhaled by the smoker. Popular smoking articles, such as cigarettes, have a substantially cylindrical rod shaped structure and include a charge, roll or column of smokable material such as shredded tobacco (e.g., in cut filler foam) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3$^{rd}$ Ed., p. 43 (1990) and *Tobacco Production, Chemistry and Technology*, Davis et al. (Eds.) p. 346 (1999).

Tobacco also may be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2005/0244521 to Strickland et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; 2008/0196730 to Engstrom et al.; 2008/0209586 to Neilsen et al.; 2008/0305216 to Crawford et al.; 2009/0025738 to Mua et al.; 2009/0025739 to Brinkley et al.; 2009/0065013 to Essen et al.; 2009/0293889 to Kumar et al.; 2010/0018540 to Doolittle et al; 2010/0018541 to Gerardi et al.; 2010/0291245 to Gao et al; 2011/0139164 to Mua et al.; 2011/0174323 to Coleman, III et al.; 2011/0247640 to Beeson et al.; 2011/0259353 to Coleman, III et al.; 2012/0037175 to Cantrell et al.; 2012/0055494 to Hunt et al.; 2012/0103353 to Sebastian et al.; 2012/0125354 to Byrd et al.; 2012/0138073 to Cantrell et al.; and 2012/0138074 to Cantrell et al; PCT WO 04/095959 to Arnarp et al.; PCT WO 05/063060 to Atchley et al.; PCT WO 05/004480 to Engstrom; PCT WO 05/016036 to Bjorkholm; PCT WO 05/041699 to Quinter et al., and PCT WO 10/132444 to Atchley; each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen moist tobacco, Copenhagen pouches, Skoal Bandits, Skoal Pouches, SkoalDry, Rooster, Red Seal long cut, Husky, and Revel Mint Tobacco Packs by U.S. Smokeless Tobacco Co.; Marlboro Snus and "taboka" by Philip Morris USA; Levi Garrett, Peachy, Taylor's Pride, Kodiak, Hawken Wintergreen, Grizzly, Dental, Kentucky King, and Mammoth Cave by American Snuff Company, LLC; Camel Snus, Camel Orbs, Camel Sticks, and Camel Strips by R. J. Reynolds Tobacco Company. Other exemplary smokeless tobacco products that have been marketed include those referred to as Kayak moist snuff and Chatanooga Chew chewing tobacco by Swisher International, Inc.; and Redman chewing tobacco by Pinkerton Tobacco Co. LP.

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. American cigarette tobacco blends typically contain a casing composition that includes flavoring ingredients, such as licorice or cocoa powder and a sugar source such as high fructose corn syrup. See also, Leffingwell et al., *Tobacco Flavoring for Smoking Products*, R.J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Pat. Appl. Pub. Nos. 2004/0173228 to Coleman, III and 2010/0037903 to Coleman, III et al., each of which is incorporated herein by reference.

The sensory attributes of smokeless tobacco can also be enhanced by incorporation of certain flavoring materials. See, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

It would be desirable to provide additional compositions and methods for altering the character and nature of tobacco (and tobacco compositions and formulations) useful in the manufacture of smoking articles and/or smokeless tobacco products. Specifically, it would be desirable to develop compositions and methods for altering the character and nature of tobacco compositions and formulations using tobacco-derived flavorful materials.

SUMMARY OF THE INVENTION

The present invention provides materials from *Nicotiana* species (e.g., tobacco-derived materials) comprising isolated components from plants of the *Nicotiana* species useful for incorporation into tobacco compositions utilized in a variety of tobacco products, such as smoking articles and smokeless tobacco products. The invention also provides methods for isolating components from *Nicotiana* species (e.g., tobacco materials), and methods for processing those components and tobacco materials incorporating those components.

In particular, the invention provides o-methylated flavonoid compounds. Surprisingly, these compounds have not been reported previously in the quantities noted herein. In one aspect of the invention is provided a method of extracting and isolating one or more o-methylated flavonoids from plants of the *Nicotiana* species, comprising: receiving a plant material of the *Nicotiana* species; contacting the plant material with a solvent for a time and under conditions sufficient to extract one or more o-methylated flavonoids from the plant material into the solvent; separating the solvent containing the one or more o-methylated flavonoids from the extracted plant material; and purifying the solvent containing the one or more o-methylated flavonoids to provide an isolate comprising at least about 50% by weight of the one or more o-methylated flavonoids on a dry weight basis.

The plant material of the *Nicotiana* species can be, in certain embodiments, in the Ruin of a leaf. In some embodiments, the the plant material of the *Nicotiana* species is provided in green form. The source of the plant material can vary, but in exemplary embodiments, the plant material of the *Nicotiana* species is obtained from a *Galpao communs* plant.

The solvent that is used for the extraction can vary. For example, in certain embodiments, the solvent comprises an alcohol solvent, e.g., methanol. In some embodiments, the solvent can consist essentially of methanol, e.g., as used in an absolute or non-absolute form (e.g., incorporating water). The solvent also can, in certain embodiments, be a co-solvent mixture of an alcohol solvent (e.g., methanol) and minor amounts of one or more solvents which are miscible therewith.

The solvent containing the one or more o-methylated flavonoids in some embodiments comprises at least about 0.2% by weight, at least about 0.5% by weight, or at least about 0.8% by weight of the one or more o-methylated flavonoids on a dry weight basis. In certain embodiments, the purifying step provides an isolate comprising at least about 70% by weight of the one or more o-methylated flavonoids or at least about 90% by weight of the one or more o-methylated flavonoids.

The specific types of o-methylated flavonoids provided according to the methods described herein can be, for example, selected from the group consisting of o-methylated kaempferol compounds, o-methylated quercetin compounds, and o-methylated luteolin compounds. Compound types include, but are not limited to: quercetin methyl ether, quercetin dimethyl ether, quercetin trimethyl ether, quercetin tetramethyl ether, quercetin pentamethyl ether, kaempferol methyl ether, kaempferol dimethyl ether, kaempferol trimethyl ether, and kaempferol tetramethyl ether. Certain exemplary compounds include, but are not limited to, quercetin methyl ethers selected from the group consisting of quercetin 3-methyl ether, quercetin 4'-methyl ether, and quercetin 4-methyl ether; quercetin 3,3',4'-trimethyl ether; and kaempferol methyl ethers selected from the group consisting of kaempferol 3-methyl ether, kaempferol 4'-methyl ether, and kaempferol 5-methyl ether.

The method can, in some embodiments, further comprise adding the isolate to a tobacco composition adapted for use in a smoking article, a smokeless tobacco product, or an aerosol-generating device that contains nicotine and/or a tobacco material or other plant material that is not combusted during use. For example, the isolate may be added in the form of a tobacco or non-tobacco material onto which the isolate is sorbed. In some embodiments, the tobacco composition is adapted for use in a smoking article and the isolate is added in the form of a casing formulation or a top dressing formulation applied to tobacco strip or in the form of a component of a reconstituted tobacco material. The amount of isolate added to the tobacco composition can be, for example, between about 5 ppm and about 5 weight percent based on the total dry weight of the tobacco material in the smoking article. In other embodiments, the isolate can be incorporated within a pharmaceutical or dietary supplement composition.

In another aspect of the invention is provided an isolate from a plant of the *Nicotiana* species or a component thereof, wherein the isolate comprises about 50% or more on a dry weight basis of one or more o-methylated flavonoids, about 70% or more on a dry weight basis of one or more o-methyl flavonoids, or about 90% or more on a dry weight basis of one or more o-methyl flavonoids. In certain embodiments, a tobacco composition is provided for use in a smoking article, a smokeless tobacco product, or an aerosol-generating device that contains nicotine and/or a tobacco material or other plant material that is not combusted during use, where the tobacco composition comprises an isolate as provided herein.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE PREFERRED EMBODIMENTS

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention provides o-methylated flavonoids extracted from a tobacco material, processes for extracting o-methylated flavonoids from a tobacco material, and products incorporating o-methylated flavonoids extracted from a tobacco material. Advantageously, the o-methylated flavonoids can be extracted from a tobacco material in significant quantities. According to the invention, o-methylated flavonoids are generally provided in the form of an extract that can be applied to a tobacco material or a non-tobacco material to enhance certain characteristics thereof. In certain embodiments, the o-methylated flavonoids are employed for their known health benefits (e.g., in dietary supplements or pharmaceutical products).

Flavonoids are generally understood to be ketone-containing compounds having two or three phenyl rings, which are secondary metabolites derived from the phenylpropanoid pathway. Generally, flavonoids can be classified as flavonols, flavones, anthocyanidins, isoflavonoids (isoflavones and isoflavonols), and neoflavonoids. Other compound classes commonly considered to be flavonoids include flavonones, anthocyanidins, catechins, dihydroflavonols, and chalcones. Naturally occurring flavonoids can be present, for example, as glycosides (bound to a sugar moiety) or as aglycones (not bound to a sugar moiety). They can, in some embodiments, be O-glycosides (having a sugar moiety bound to an oxygen atom) or C-glycosides (having a sugar moiety bound to a carbon atom) and, unless otherwise noted, reference herein to flavonoids is intended to cover both glycoside (O-glycoside and C-glycoside) and aglycone forms.

It has been reported that over 8,000 different flavonoids have been isolated and identified from various plant sources. Exemplary flavonoids previously noted in certain *Nicotiana* species include, but are not limited to, rutin, apigenin, quercetin, and isoquercetin. See, for example, Kaushik et al., *J. Pharm. Res.* (2010), 3(5): 1144-1145; Fathiazad et al., *Ir. J. Pharm. Res.* (2006) 3:222-227; Wollenweber et al., *Z. Naturforsch* (2005) 60c: 661-670; and Roda et al., *Phytochemistry* (2003) 62: 527-536, which are incorporated herein by reference.

O-methylated flavonoids are flavonoids wherein one or more of the hydroxyl groups is replaced by a methoxy (O-methyl) group. O-methylated flavonoids are generally formed by the action of O-methyltransferase enzymes on flavonoids. Only very small amounts of o-methylated flavonoids have been previously found to be present in tobacco materials. See, for example, Rodgman, A. et al., The Chemical Components of Tobacco and Tobacco Smoke (2009), CRC Press, pg. 524; Roda et al., *Phytochemistry* (2003) 62: 527-536; Yang et al., Tso, T. C., Production, Physiology, and Biochemistry of Tobacco Plant (1990), Ideals, Inc. pg. 600; J. Org. Chem. (1960) 25(11): 2063-2064; and Frankenburg, W. G.; Southern Chemist, March Issue (1949), pg. 315-330, which are all incorporated herein by reference. In fact, in the plant kingdom generally, these compounds are found in very small quantities (typically, less than about 0.01% by weight where found).

According to certain embodiments of the present invention, o-methylated flavonoids that are advantageously extracted and isolated from tobacco materials are flavonols (e.g., o-methylated quercetins, o-methylated kaempferols, and analogues and isomers thereof). Other o-methylated flavonoids that can be extracted and isolated include o-methylated flavanonols (e.g., o-methylated dihydrokaempferol) and o-methylated flavones (e.g., o-methylated luteolin). In certain embodiments, significant amounts of o-methylated flavonoids can be obtained from a tobacco plant (e.g., in the form of an extract from a tobacco plant or portion thereof).

The products of the disclosure incorporate some form of a plant of the *Nicotiana* species, and most preferably, those compositions or products incorporate some foam of tobacco. The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). Additional information on types of *Nicotiana* species suitable for use in the present invention can be found in US Pat. Appl. Pub. No. 2012/0192880 to Dube et al., which is incorporated by reference herein. Tobacco plants can be grown in greenhouses, growth chambers, or outdoors in fields, or grown hydroponically.

The *Nicotiana* species can be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. In some embodiments, *Galpao commun* and other types of plants having "sticky" leaves (e.g., Oriental varieties) are particularly preferred. In certain embodiments, *Nicotiana glutonisa* may be used.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *Nicotiana* species. See, for example, the portions of tobacco plants set forth in US Pat. Appl. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green form or a cured form, as described in 2012/0192880 to Dube et al., which is incorporated by reference herein. The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. Exemplary processing techniques are described, for example, in US Pat. Appl. Pub. Nos. 2009/0025739 to Brinkley et al. and 2011/0174323 to Coleman, III et al., which are incorporated by reference herein.

At least a portion of the plant of the *Nicotiana* species can be treated with enzymes and/or probiotics before or after harvest, as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant. As such, harvested portion or portions of the plant can be used as such as components of tobacco products, or processed further.

In certain embodiments, the portion or portions of the plant of the *Nicotiana* species are treated so as to provide one or more components contained therein in a more usable (e.g., more concentrated) form. Various compounds or mixtures of compounds from the *Nicotiana* plant or portions thereof can be isolated by the methods provided herein. As used herein, an "isolated component," or "plant isolate," is a compound or complex mixture of compounds separated from a plant of the *Nicotiana* species or a portion thereof. The isolated component can be a single compound, a homologous mixture of similar compounds (e.g., isomers of a flavor compound), or a heterologous mixture of dissimilar compounds (e.g., a complex mixture of various compounds of different types, preferably having desirable sensory attributes). See, for example, the description of isolated tobacco components and techniques for isolation in US Pat. Appl. Pub. Nos. 2011/0174323 to Coleman, III et al.; 2011/0259353 to Coleman, III et al.; 2012/0192880 to Dube et al.; 2012/0192882 to Dube et al.; and 2012/0211016 to Byrd, Jr. et al., which are incorporated by reference herein.

A desired component or a mixture of desired components can be isolated from a plant of the *Nicotiana* species by various means. Typical separation processes can include one or more process steps such as solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning. In some embodiments, plant or portion of the *Nicotiana* species is pre-treated, e.g., to liberate certain compounds to make the desired compounds available for more efficient separation. In some embodiments, multiple methods are used to isolate and/or purify the desired compounds.

In some embodiments, isolated compounds or mixtures thereof can be subjected to conditions so as to cause those compounds to undergo chemical transformation. For example, the tobacco material obtained from plants of the *Nicotiana* species or portion thereof can be treated to cause chemical transformation or be admixed with other ingredients. In some embodiments, the extracts obtained therefrom, or the isolated compound(s) (isolates) can be treated to cause chemical transformation or be admixed with other ingredients. The chemical transformations or modification of the tobacco material, extract, or isolated compound can result in changes of certain chemical and physical properties of the tobacco material, extract, or isolated compound(s) (e.g., the sensory attributes thereof). Exemplary chemical modification processes can be carried out by acid/base reaction, hydrolysis, oxidation, heating and/or enzymatic treatments; and as such, compounds can undergo various degradation reactions. Exemplary chemical transformation techniques are set forth in US Pat. Appl. Pub. Nos. 2011/0174323 to Coleman, III, et al. and 2011/0259353 to Coleman, III et al., which are incorporated by reference herein.

In certain embodiments, the tobacco material, extract, or isolate is treated to provide degradation products. Degradation products are any compounds that are produced from the compounds extracted and/or isolated according to the present invention. Degradation products can be formed naturally from such compounds or may be produced by an accelerated degradation process (e.g., by the addition of heat and/or chemicals to accelerate the breakdown of the compounds). These compounds can be degraded, for example, by means of oxidation (e.g., through treatment with $H_2O_2$ or other oxidizing agents) and/or hydrolysis reactions.

Although in some embodiments, the tobacco material, extract, or isolate is used directly, it may be desirable to thermally treat the tobacco material, extract, or isolate in order to, for example, pasteurize the material or otherwise chemically alter the material. This thermal treatment can be conducted before or after any of the processes described herein for the isolation of one or more components from a plant of the *Nicotiana* species. For example, a tobacco material can be thermally processed by mixing the tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents (e.g., hydrogen peroxide), oxidation catalysts, plant extracts, and combinations thereof, to form a moist tobacco mixture; and heating the moist tobacco mixture at a temperature of at least about 60° C. to form a heat-treated tobacco mixture. In one embodiment, the treated tobacco extract is heat treated in the presence of water, NaOH, and an additive (e.g., lysine) at about 88° C. for about 60 minutes. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference. In certain embodiments wherein a heat-treated tobacco isolate is used in a smokeless tobacco product of the present invention, the product can be characterized by very low acrylamide content. For example, in some embodiments, the smokeless tobacco product is characterized by an acrylamide content of less than about 500 ppb (ng/g), less than about 400 ppb, less than about 300 ppb, less than about 200 ppb, or less than about 100 ppb.

Following one or more of the methods disclosed herein for the isolation of one or more components from a plant of the *Nicotiana* species, any liquid material thus obtained can be further processed if desired. For example, the liquid can be processed in a manner adapted to concentrate the dissolved or dispersed components of the liquid by removing at least a portion of the solvent (e.g., water). The concentration step removes water from the extracted aqueous liquid, which can provide a powder having an increased concentration of various compounds.

The tobacco material can also be subjected to further treatment steps, which can be used in the place of, or in addition to, the other isolation steps described herein. For example, in some embodiments, the isolate is brought into contact with an imprinted polymer or non-imprinted polymer such as described, for example, in US Pat. Pub. Nos. 2007/0186940 to Bhattacharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted or non-imprinted polymer can be used to remove certain components of the extract, such as tobacco-specific nitrosamines (TSNAs), including N'-nitrosonomicotine (NNN), (4-methylnitrosamino)-1-(3-pyridyl)-1-butanone (NNK), N'-nitrosoanatabine (NAT), and N'-nitrosoanabasine (NAB); polyaromatic hydrocarbons (PAHs), including benz[a]anthracene, benzo[a]pyrene, benzo[b]fluoranthene, benzo[k]fluoranthene, chrysene, dibenz[a,h]anthracene, and indeno[1,2,3-cd]pyrene; or other Hoffmann analytes.

In certain embodiments, solvent extraction is used to isolate a desired component or a mixture of desired components from a plant of the *Nicotiana* species. Exemplary extraction and separation solvents or carriers include water, alcohols (e.g., methanol or ethanol), hydrocarbons (e.g., heptane and hexane), diethyl ether, methylene chloride, supercritical carbon dioxide, and combinations thereof. In certain embodiments, a solvent comprising one or more alcohols, e.g., methanol, is used. In some embodiments, the solvent can consist essentially of methanol, e.g., as used in an absolute or non-absolute form (e.g., incorporating water). The solvent also can, in certain embodiments, be a co-solvent mixture of an alcohol solvent (e.g., methanol) and minor amounts of one or more solvents which are miscible therewith. Exemplary techniques useful for extracting components from *Nicotiana* species are described or referenced in U.S. Pat. No. 5,065,775 to Fagg; and Appl. Pub. Nos. 2011/0259353 to Coleman, III et al. and 2012/0211016 to Byrd, Jr. et al., which are incorporated by reference herein.

The conditions of the extraction process can vary. In some embodiments, the plant of the *Nicotiana* species is combined with a solvent to form a material (e.g., in the form of a suspension or slurry). In certain embodiments, the amount of solvent added to form the moist material can be at least about 50 weight percent, or at least about 60 weight percent, or at least about 70 weight percent, based on the total weight of the material. In some cases, the amount of solvent can be described as at least about 80 weight percent or at least about 90 weight percent.

Various reagents can be added to the extraction solvent. In some embodiments, a processing aid is added to facilitate the extraction. A processing aid is any agent that facilitates the extraction of the desired component(s) into the extraction solvent. For example, suitable processing aids include, but are not limited to, mineral acids and enzymes. Various other additives can be used in the extraction process, including, but not limited to, surfactants and co-solvents.

The amount of time required to effectuate extraction is partially dependent on the temperature and pressure at which the extraction is conducted. For example, in some embodiments, heating the material to an elevated temperature and/or pressurizing the material increases the rate of extraction. The time range for the extraction process is typically at least about 30 minutes (e.g., at least about 1 hour or at least about 2 hours) and typically less than about 24 hours (e.g., less than about 12 hours or less than about 8 hours), although other time periods could be used without departing from the invention. In some embodiments, multiple extractions can be conducted to extract additional compounds therefrom. See, for example, US Patent App. Publ. No. 2008/0254149 to Havkin-Frenkel, which is incorporated herein by reference.

In certain embodiments, the extract comprises a substantial quantity of o-methylated flavonoids. It may comprise some mixture of o-methylated flavonols, o-methylated flavones, o-methylated anthocyanidins, o-methylated isoflavonoids (isoflavones and isoflavonols), and o-methylated neoflavonoids. The o-methylated flavonoids can be present as glycosides or as aglycones. In some embodiments, the amount of o-methylated flavonoids in an extract according to the invention is at least about 0.1% of the extracted compounds on a dry weight basis (e.g., between about 0.1 and about 1.5% of the extracted compounds on a dry weight basis). In certain embodiments, extracts can comprise about 0.3% or more, about 0.5% or more, about 0.8% or more, or about 1% or more o-methylated flavonoids on a dry weight basis (e.g., about 1%). In certain embodiments, the o-methylated flavonoid-containing extract is a methanol extract, although other solvents (e.g., other alcohol solvents) could be used.

In some embodiments, multiple sequential separation processes can be employed to purify and refine a sample in the desired manner. For example, a solvent extract or distillate can, in some embodiments, be subjected to additional separation steps to change the chemical composition of the extract or distillate, such as by increasing the relative amount of certain desirable compounds, such as certain flavorful or aromatic compounds. In some embodiments, an extract or distillate can be treated by filtration. As another example, one of the processes noted above (e.g., solvent extraction or distillation) may be combined with one or more chromatographic methods. In some embodiments, a sample is first treated to remove one or more compounds that are known to elute under similar conditions as the compound(s) to be isolated by flash chromatography. In other embodiments, a sample can be dissolved and directly subjected to chromatographic separation.

In some embodiments, preparative liquid chromatography is used to isolate and/or purify certain compounds of interest from a tobacco material (e.g., from a tobacco extract or distillate). In some embodiments, a compound or compounds of interest are isolated using preparative liquid chromatography based on the elution times of standards. Various automated commercial prep-LC systems are available, from manufacturers including Waters, Agilent Technologies, and Bio-Rad. The specific parameters of the prep LC system used can be varied by one of skill in the art to achieve the desired level of resolution. For example, the solvent may be any solvent or mixture of solvents sufficient to dissolve the compound(s) of interest. The solvent may be, for example, water, methanol, ethanol, ethyl acetate, diethyl ether, methylene chloride, chloroform, petroleum ether, and/or hexanes. The system may be operated with an isocratic or gradient solvent system (i.e., varying the ratio of two or more solvents as a function of time). In some embodiments, the solvent system can be chosen such that it provides the best resolution between the compound of interest and other compounds present in the mixture. The flow rate of the system may be varied, for example, from about 10 mL/min to about 100 mL/min (e.g., about 36 mL/min).

In some embodiments, flash chromatography is used to isolate and/or purify certain compounds of interest from a tobacco extract. Flash chromatography systems are known in the art and exemplary systems are discussed, for example, in Still et al., J. Org. Chem. 42: 2923-2925 (1978) and U.S. Pat. No. 4,591,442 to Andrews, which are incorporated herein by reference. Various automated commercial flash chromatography systems are available, from manufacturers including Biotage, Teledyne Isco, Grace Davison Discovery Sciences, and Buchi. Flash chromatography may be desirable to provide reasonably large quantities of compound, as columns typically have relatively large particle sizes (e.g., roughly 30-40 μm) and can accommodate a greater quantity of sample (and a more concentrated sample), allowing more of the compound(s) of interest to be isolated per injection.

The specific parameters of the flash chromatography system used can be varied by one of skill in the art to achieve the desired level of resolution. For example, the solvent may be any solvent or mixture of solvents sufficient to dissolve the compound(s) of interest. The solvent may be, for example, water, methanol, ethanol, ethyl acetate, diethyl ether, methylene chloride, chloroform, petroleum ether, and/or hexanes. The system may be operated with an isocratic or gradient solvent system (i.e., varying the ratio of two or more solvents as a function of time). In some embodiments, the solvent system may be chosen to provide the best resolution between the compound of interest and other compounds present in the mixture. The flow rate of the system may be varied, for example, from about 20 to about 200 mL/min (e.g., about 150 mL/min).

Flash chromatography may or may not provide the compound(s) of interest at a sufficient purity level. In certain embodiments, the fractions corresponding to the compound(s) of interest may be collected, combined, and concentrated to give an isolate comprising the compound(s) of interest at a sufficient level of purity (i.e., wherein the compound(s) of interest are present in a sufficient weight percentage of the isolate). For example, the isolate of the present invention can comprise the compound(s) of interest in an amount of greater than about 75% by weight, greater than about 80% by weight, greater than about 85% by weight, greater than about 90% by weight, greater than about 95% by weight, greater than about 98% by weight, or greater than about 99% by weight. In some embodiments, fractions obtained from flash chromatography can be further resolved using preparative liquid chromatography.

Various methods of solvent removal can be employed, such as heat treatment to evaporate the solvent, reverse osmosis membrane treatment, spray drying or freeze drying. In one embodiment, the concentration process can entail heating the extracted liquid in a vented vessel to evaporate a portion of the water. The temperature and pressure at which the liquid is heated may vary. See, for example, the solvent removal techniques set forth in US Pat. Pub. No. 2012/0152265 to Dube et al., which is incorporated by reference herein.

The form of the tobacco isolate obtained according to the present invention can vary. Typically, the isolate is in a solid, liquid, or semi-solid or gel foam. The formulation can be used in concrete, absolute, or neat form. Solid forms of the tobacco isolate can include spray-dried and freeze-dried forms. Liquid forms of the tobacco isolate can include formulations contained within aqueous or organic solvent carriers.

The tobacco isolate can comprise various quantities of one or more o-methylated flavonoids. In certain embodiments, the tobacco isolate contains a single o-methylated flavonoid. In other embodiments, the tobacco isolate contains a mixture of o-methylated flavonoids. For example, in certain embodiments, o-methylated analogues of quercetin, kaempferol, and/or luteolin are present in the extracts and isolates described herein.

The o-methylated flavonoids extracted according to the methods described herein and present in the extracts and isolates described herein can vary. At least one O-methyl group is present on the flavonoids; however, the position of the at least one O-methyl group can vary. The number of o-methylated moieties can also vary; for example, in certain embodiments, one, two, three, four, or five O-methyl moieties are present on the flavonoid. Certain exemplary flavonoids that can be obtained according to the invention include, but are not limited to, quercetin methyl ether (e.g., quercetin 3-methyl ether, quercetin 4'-methyl ether, quercetin 4-methyl ether), quercetin dimethyl ether, quercetin trimethyl ether (e.g., quercetin 3,3',4'-trimethyl ether), quercetin tetramethyl ether, quercetin pentamethyl ether, kaempferol methyl ether (e.g., kaempferol 3-methyl ether, kaempferol 4'-methyl ether, kaempferol 5-methyl ether), kaempferol dimethyl ether, kaempferol trimethyl ether, and kaempferol tetramethyl ether.

Isolates prepared according to the invention can have varying levels of purity. For example, in certain embodiments, an isolate comprising a single o-methylated flavonoid is provided in at least about 50% purity, at least about 60% purity, at least about 70% purity, at least about 80% purity, at least about 90% purity, or at least about 95% purity by weight on a dry weight basis. In some embodiments, these purity levels are intended to apply to any specific o-methylated flavonoids, including those specifically listed above. In some embodiments, the isolate may comprise more than one o-methylated flavonoid, where the isolate contains at least about 50%, at least about 60%, at least about 70%, at least about 80%, at least about 90%, or at least about 95% by weight of the more than one o-methyl flavonoid. In other words, isolates prepared according to the invention can comprise primarily one or more o-methylated flavonoid. Again, these purities in some embodiments apply to any o-methylated flavonoids, including those listed in the paragraph above. Exemplary isolates can comprise less than about 50%, less than about 40%, less than about 30%, less than about 20%, less than about 10%, or less than about 5% impurities (i.e., compounds other than o-methylated flavonoids).

Tobacco isolates generated according to the process of the invention are useful as materials for various compositions. Although the use of such tobacco isolates is generally described in the context of tobacco compositions, it is noted that such formulations can be applicable in many other types of compositions.

In some embodiments, the tobacco extracts and isolates described herein are incorporated within tobacco compositions, particularly tobacco compositions incorporated into smoking articles or smokeless tobacco products. In accordance with the present invention, a tobacco product incorporates tobacco that is combined with one or more tobacco-derived isolates according to the invention. That is, a portion of the tobacco product can be comprised of some form of tobacco isolate formulation prepared according to the invention. In some embodiments, the tobacco extract or isolate is sorbed onto a tobacco material. In certain embodiments, the extracts or isolates of the invention can be added to a non-tobacco material.

The non-tobacco material can be any material obtained from a source other than a plant of the *Nicotiana* species. For example, possible non-tobacco materials upon which the extracts or isolates of the invention can be sorbed include, bur are not limited to, pulp from vegetables, fruits, or other fibrous plant materials (e.g., processed sugar beet pulp or cellulosic materials), pulp obtained after removal of water soluble components as a result of water extraction treatment, or a combination thereof. Note that the term "sorb" as used herein refers to incorporation of the aqueous tobacco extract into a substrate (i.e., a tobacco material or a non-tobacco material) by any known process including absorption and adsorption.

Addition of the tobacco isolate described herein to a tobacco composition can enhance a tobacco composition in a variety of ways, depending on the nature of the tobacco isolate and the type of tobacco composition. Exemplary isolates can serve to provide flavor and/or aroma to a tobacco product (e.g., the composition can alter the sensory characteristics of tobacco compositions or smoke derived therefrom). Other isolates can serve functional purposes within tobacco compositions, such as binder or filler functions. Certain isolates can serve as a replacement for one or more traditional components of a tobacco product. For example, in certain embodiments, extracts and isolates of the invention can be described as providing a flavor and aroma reminiscent of Oriental tobaccos.

The tobacco product to which the tobacco isolates of the invention are added can vary, and may include any product configured or adapted to deliver tobacco or some component thereof to the user of the product. Exemplary tobacco products include smoking articles (e.g., cigarettes), smokeless tobacco products, and aerosol-generating devices that contain nicotine and/or a tobacco material or other plant material that is not combusted during use. The incorporation of the tobacco isolates of the invention into a tobacco product may involve use of a tobacco material or non-tobacco plant material as a carrier for the formulations, such as by absorbing the isolate into the tobacco or other plant material or otherwise associating the isolate with the carrier material (as described in greater detail above). The types of tobacco that can serve as the carrier for the formulations of the invention can vary, and can include any of the tobacco types discussed herein, including various cured tobacco materials (e.g., flue-cured or air-cured tobaccos) or portions thereof (e.g., tobacco lamina or tobacco stems). The physical configuration of the tobacco material to which the formulation is added can also vary, and can include tobacco materials in shredded or particulate form, or in the form of a sheet (e.g., reconstituted tobacco sheets) or in whole leaf form.

Accordingly, tobacco isolates provided herein can, in some embodiments, be used as compositions in the manufacture of smoking articles. For example, the formulations prepared in accordance with the present invention can be mixed with casing materials and applied to tobacco as a casing ingredient or as a top dressing. Still further, the formulations of the invention can be incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Figure 1:
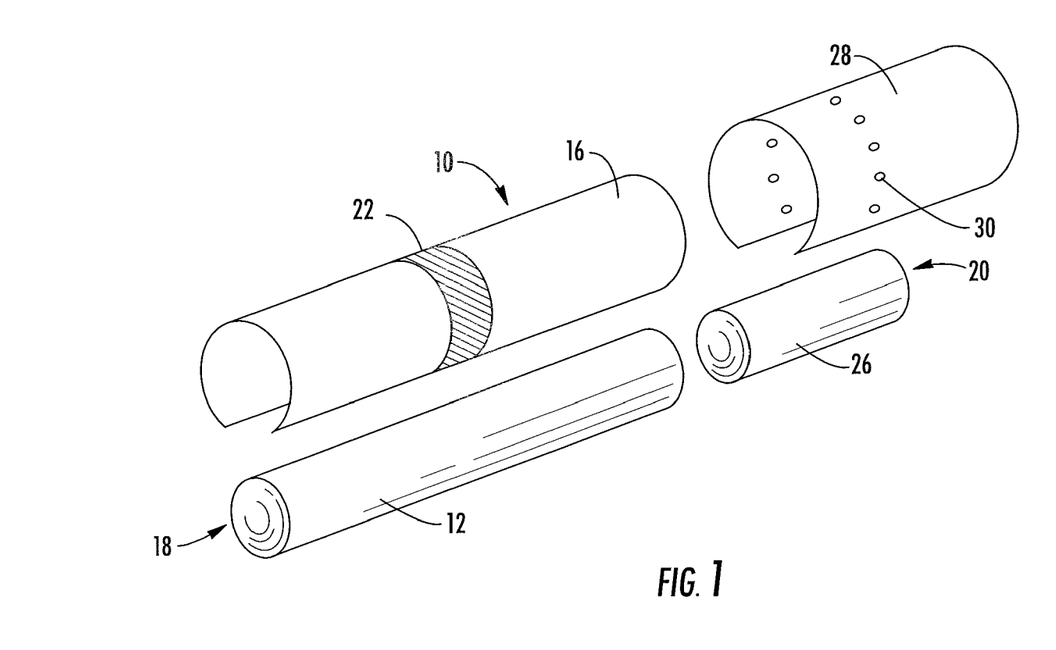
FIG. 1 is an exploded perspective view of a smoking article having the form of a cigarette, showing the smokable material, the wrapping material components, and the filter element of the cigarette.

Referring to FIG. 1, there is shown a smoking article 10 in the form of a cigarette and possessing certain representative components of a smoking article that can contain the formulation of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethyl cellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The formulations of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

The formulations of the invention can also be incorporated into aerosol-generating devices that contain nicotine and/or tobacco material (or some portion or component thereof) that is not intended to be combusted during use, including so-called "e-cigarettes". Some of these types of smoking articles employ a combustible fuel source that is burned to provide an aerosol and/or to heat an aerosol-forming material. Others employ battery-powered heating elements to heat an aerosol-forming composition. Exemplary references that describe smoking articles of a type that generate flavored vapor, visible aerosol, or a mixture of flavored vapor and visible aerosol, include those set forth in US Pat. Pub. No. 2012/0192880 to Dube et al., which is incorporated by reference herein.

The formulations of the invention can be incorporated into smokeless tobacco products, such as loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. Various types of smokeless tobacco products are described or referenced in US Pat. Pub. No 2012/0152265 to Dube et al., which is incorporated herein by reference.

Figure 2:
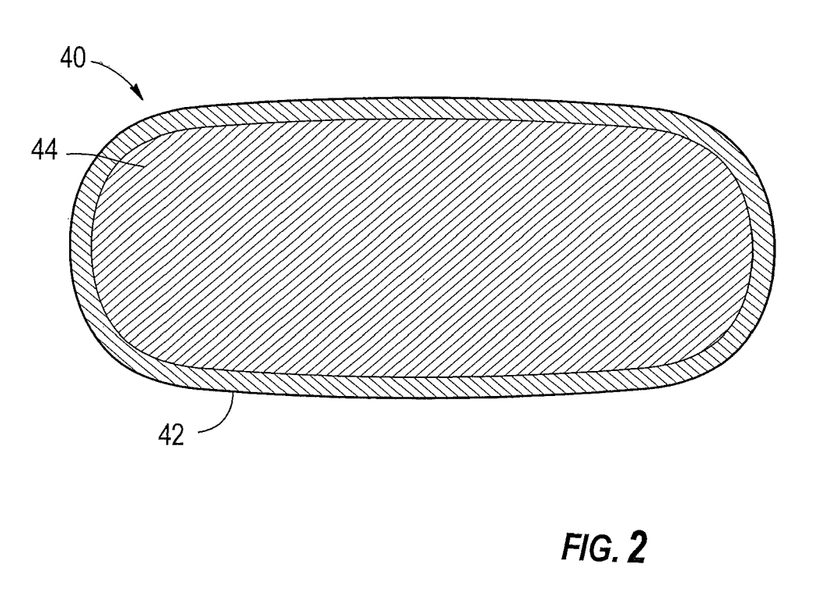
FIG. 2 is a cross-sectional view of a smokeless tobacco product embodiment, taken across the width of the product, showing an outer pouch filled with a smokeless tobacco composition of the invention.

Referring to FIG. 2, a representative snus type of tobacco product comprising a formulation of the present invention is shown. In particular, FIG. 2 illustrates a smokeless tobacco product 40 having a water-permeable outer pouch 42 containing a smokeless tobacco composition 44. Any of the components of the tobacco product can comprise a tobacco isolate as described herein (e.g., the interior or exterior of the pouch lining or a portion of the smokeless tobacco composition contained therein).

Many exemplary smokeless tobacco compositions that can benefit from use of the formulations of the invention comprise shredded or particulate tobacco material that can serve as a carrier for the tobacco isolates of the invention. The smokeless tobacco compositions of the invention can also include a water-soluble polymeric binder material and optionally other ingredients that provide a dissolvable composition that will slowly disintegrate in the oral cavity during use. In certain embodiments, the smokeless tobacco composition can include lipid components that provide a meltable composition that melts (as opposed to merely dissolving) in the oral cavity, such as compositions set forth in US Pat. Pub. No. 2012/0037175 to Cantrell et al., which is incorporated by reference herein.

In one particular smokeless tobacco product embodiment, a composition of the invention is added to a non-tobacco plant material, such as a plant material selected from potato, beet (e.g., sugar beet), grain, pea, apple, and the like. The non-tobacco plant material can be used in a processed form. In certain preferred embodiments, the non-tobacco plant material can be used in an extracted form, and as such, at least a portion of certain solvent soluble components are removed from that material. The non-tobacco extracted plant material is typically highly extracted, meaning a substantial amount of the aqueous soluble portion of the plant material has been removed. See, for example, US Pat. Pub. No. 2011/0247640 to Beeson et al, which is incorporated by reference herein.

Further ingredients can be admixed with, or otherwise incorporated within, the smokeless tobacco compositions according to the invention. The ingredients can be artificial, or can be obtained or derived from herbal or biological sources. Exemplary types of ingredients include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like), binders (e.g., povidone, sodium carboxymethylcellulose and other modified cellulosic types of binders, sodium alginate, xanthan gum, starch-based binders, gum arabic, lecithin, and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), colorants (e.g., dyes and pigments, including caramel coloring and titanium dioxide, and the like), humectants (e.g., glycerin, propylene glycol, and the like), effervescing materials such as certain acid/base combinations, oral care additives (e.g., thyme oil, eucalyptus oil, and zinc), preservatives (e.g., potassium sorbate, and the like), syrups (e.g., honey, high fructose corn syrup, and the like), disintegration aids (e.g., microcrystalline cellulose, croscarmellose sodium, crospovidone, sodium starch glycolate, pregelatinized corn starch, and the like), flavorant and flavoring mixtures, antioxidants, and mixtures thereof. Exemplary encapsulated additives are described, for example, in WO 2010/132444 to Atchley, which has been previously incorporated by reference herein. See also, the smokeless tobacco ingredients set forth in US Pat. Pub. Nos. 2012/0055494 to Hunt et al. and 2012/0199145 to Byrd et al., which are incorporated by reference herein.

The amount of the tobacco isolate of the present invention incorporated within a tobacco composition or tobacco product can depend on the desired function of the isolate, the chemical makeup of the isolate, and the type of tobacco composition to which the isolate is added. The amount of tobacco isolate added to a tobacco composition can vary, but will typically not exceed about 50 weight percent based on the total dry weight of the tobacco composition to which the composition is added. For example, the amount of tobacco isolate added to a tobacco composition may be in the range of about 0.25 to about 25 weight percent or about 1 to about 10 weight percent, based on the total dry weight of the tobacco composition.

The isolated o-methyl flavonoids provided according to the methods of the present application may also find use outside the field of tobacco products. For example, certain flavonoids are recognized for their potential benefits to the ecology of plants. Certain flavonoids can provide benefits in protecting against UV light, warding off pathogenic microorganisms and other pests, promoting fertility and germination of pollen, activating bacterial nodulation genes, and regulating plant growth and enzyme activity.

Flavonoids are generally recognized for their health benefits to humans and animals and may be incorporated as components of pharmaceuticals and/or dietary supplements (understood to encompass products containing a dietary ingredient and intended to supplement the diet, which are intended for ingestion in pill, capsule, tablet, powder, or liquid form, and not represented for use as a conventional food). Flavonoids contribute to the nutritional qualities of fruits and vegetables. Flavonoids have been reported to provide antioxidant activity toward free radicals and reactive oxygen species and have shown oestrogenic and anticancer activity (e.g., antiproliferation, promotion of differentiation and apoptosis). Other reports have noted anti-inflammatory, antiulcerogenic, antidiabetic, antiallergic, antiviral, antibacterial, antifungal, anxiolytic, antineoplastic, antithrombogenic, and antiatherosclerotic effects. Flavonoids have further been suggested to play a protective role in liver disease, cataracts, and cardiovascular disease. See, for example, Kumar et al., Int. Pharm. Sciencia (2011) 1(1): 25-41; Cui et al., Cancer (2008) 112(10): 2241-2248 and Tapas., A., Pharm. Res. (2008), 7 (September): 1089-1099 and references cited therein, which are incorporated herein by reference.

O-methylated flavonoids can exhibit such benefits and can be used for these purposes. In fact, it has been found that, in comparison with non-methylated analogues, certain o-methylated flavonoids exhibit superior metabolic stability, intestinal absorption, and transport. See Bernini et al., Molecules (2011) 16(2): 1418-1425; Wen et al., Drug Metabolism & Disposition (2006), 34: 1786-1792; Spencer, J. Nutr. (2003), 133(10): 32555-32615, which are incorporated herein by reference. Noting these advantages, various synthetic routes to o-methylated flavonoids have been proposed (i.e., by methylating one or more hydroxy groups of natural flavonoids). The present invention directly provides relatively pure isolates of one or more naturally occurring o-methylated flavonoids.

According to the invention, tobacco-derived isolates of one or more o-methyl flavonoids can be incorporated within dietary supplements or pharmaceutical formulations by any means known in the art. The isolates can be directly introduced into the formulation or can be sorbed onto another type of material (e.g., a plant material such as cellulose) prior to incorporation within the formulation. The o-methylated flavonoid isolate is generally provided in an amount sufficient to elicit some desired effect. In some embodiments, one or more additional biologically active compounds are incorporated within the same pharmaceutical or dietary supplement composition. Typically, in addition to the isolates described herein, pharmaceutical and dietary supplement compositions comprise various pharmaceutically acceptable excipients and additives (e.g., sugars, sugar substitutes, starches, fillers, salts, flavorants, buffering agents, preservatives, etc). For an overview of various considerations in pharmaceutical production, see, for example, Remington's Pharmaceutical Sciences (18$^{th}$ ed.; Mack Publishing Company, Eaton, Pa., 1990), which is incorporated herein by reference in its entirety.

EXPERIMENTAL

Aspects of the present invention is more fully illustrated by the following example, which is set forth to illustrate certain aspects of the present invention and is not to be construed as limiting thereof.

A methanol extract of green leaf *Galpao Commun* tobacco is obtained. A crude mass spectrometry analysis indicates several highly intense mass peaks that do not correspond to known compounds in tobacco (at masses of 299.06, 313.07, 315.05, 327.05, 329.07, 341.11, and 343.10). To further evaluate the makeup of the extract, 0.1 gram of the extract is added to a flask containing 10 mL of MeOH. The mixture is agitated for 30 minutes at 250 rpm on an orbital shaker. The MeOH extract is then filtered through a Whatman 0.45 µm filter syringe into LC vials for analysis.

Qualitative analysis of the unidentified compounds in the MeOH extract is performed on a Waters Acquity UPLC coupled to a Thermo LTQ-Orbitrap High Resolution Mass Spectrometer in negative electrospray ionization mode. Enhanced extracted ion chromatograms are generated by selecting a small isolation mass width in the spectrum and applying that mass width across the chromatograph (e.g., for the mass peak 329.0697, the width selected for the extracted ion chromatogram was 329.0690-329.0710). For this sample, three chromatic peaks are observed. Although not intending to be limited by theory, it is believed that the three peaks correspond to three different isomers or varying positions of methoxylation.

To confirm the substructures, the MS2 and MS3 fragmentation patterns for the unknown masses are compared against MS2 and MS3 fragmentation patterns for high purity standard samples (obtained from Sigma-Aldrich) of 3-O-methyl quercetin, isorhamnetin (quercetin analog), rhamnetin (quercetin analog) and kaempferide (kaempferol analog). In the MS2 experiments, the standards, as well as the extracted compounds, show a mass loss from the parent mass corresponding to a methyl group and neutral charge. This pattern is consistent with the predicted nature of O-methylated flavonoids. The results of the MS3 experiments reveal similar fragmentation patterns as well. In all cases, the unknown mass peaks and the predicted empirical formulas for the methoxylated flavonoids are within 7 ppm, which indicates that the predicted empirical formulas are a high probably match.

To estimate the concentration of each compound in the extract, the area counts exhibited in the present experiment from extracted ion chromatograms are compared with known area counts for sucrose esters in Oriental tobacco samples. Based on rutin external calibration curves generated during the known run sequence, the known area counts correspond to concentrations in the range of 0.1-0.2% of the leaf dry weight. It is known that such Oriental tobacco leaves are approximately 4 to 5 fold less concentrated in leaf surface chemistry than *Galpao Commun*, and it follows that the concentration of compounds in the extract (o-methylated flavonoids) would be about 1% on a dry weight basis or greater.

What is claimed:

1. A method of extracting and isolating one or more o-methylated flavonoids from plants of the *Nicotiana* species, comprising:
   receiving a plant material of the *Nicotiana* species;
   contacting the plant material with a solvent for a time and under conditions sufficient to extract one or more o-methylated flavonoids from the plant material into the solvent, wherein the solvent is methanol;
   separating the solvent containing the one or more o-methylated flavonoids from the extracted plant material, wherein the solvent containing the one or more o-methylated flavonoids contains at least about 0.1% of the o-methylated flavonoids on a dry weight basis; and
   purifying the solvent containing the one or more o-methylated flavonoids to provide an isolate comprising at least about 50% by weight of the one or more o-methylated flavonoids on a dry weight basis.

2. The method of claim 1, wherein the plant material of the *Nicotiana* species is in the form of a leaf.

3. The method of claim 1, wherein the plant material of the *Nicotiana* species is provided in green form.

4. The method of claim 1, wherein the plant material of the *Nicotiana* species is obtained from a *Galpao communs* plant.

5. The method of claim 1, wherein the solvent containing the one or more o-methylated flavonoids comprises at least about 0.2% by weight of the one or more o-methylated flavonoids on a dry weight basis.

6. The method of claim 1, wherein the solvent containing the one or more o-methylated flavonoids comprises at least about 0.5% by weight of the one or more o-methylated flavonoids on a dry weight basis.

7. The method of claim 1, wherein the solvent containing the one or more o-methylated flavonoids comprises at least about 0.8% by weight of the one or more o-methylated flavonoids on a dry weight basis.

8. The method of claim 1, wherein the purifying step provides an isolate comprising at least about 70% by weight of the one or more o-methylated flavonoids.

9. The method of claim 1, wherein the purifying step provides an isolate comprising at least about 90% by weight of the one or more o-methylated flavonoids.

10. The method of claim 1, wherein the one or more o-methylated flavonoids are selected from the group consisting of o-methylated kaempferol compounds, o-methylated quercetin compounds, and o-methylated luteolin compounds.

11. The method of claim 1, wherein the one or more o-methylated flavonoids are selected from the group consisting of quercetin methyl ether, quercetin dimethyl ether, quercetin trimethyl ether, quercetin tetramethyl ether, quercetin pentamethyl ether, kaempferol methyl ether, kaempferol dimethyl ether, kaempferol trimethyl ether, and kaempferol tetramethyl ether.

12. The method of claim 11, wherein the quercetin methyl ether is selected from the group consisting of quercetin 3-methyl ether, quercetin 4'-methyl ether, quercetin 4-methyl ether; the quercetin trimethyl ether is quercetin 3,3',4'-trimethyl ether; and the kaempferol methyl ether is selected from the group consisting of kaempferol 3-methyl ether, kaempferol 4'-methyl ether, and kaempferol 5-methyl ether.

13. The method of claim 1, further comprising adding the isolate to a tobacco composition adapted for use in a smoking article, a smokeless tobacco product, or an aerosol-generating device that contains nicotine or a tobacco material or other plant material that is not combusted during use.

14. The method of claim 13, wherein the isolate is sorbed onto tobacco or a non-tobacco material.

15. The method of claim 13, wherein the tobacco composition is adapted for use in a smoking article and the isolate is added in the form of a casing formulation or a top dressing formulation applied to tobacco strip or in the form of a component of a reconstituted tobacco material.

16. The method of claim 13, wherein the amount of the isolate in the tobacco composition is between about 5 ppm and about 5 weight percent based on the total dry weight of the tobacco material in the smoking article.

17. The method of claim 1, further comprising incorporating the isolate within a pharmaceutical or dietary supplement composition.

18. The method of claim 1, wherein the solvent containing the one or more o-methylated flavonoids contains about 1% or more of the o-methylated flavonoids on a dry weight basis.

* * * * *

UNITED STATES PATENT AND TRADEMARK OFFICE
CERTIFICATE OF CORRECTION

PATENT NO. : 11,412,775 B2
APPLICATION NO. : 13/647670
DATED : August 16, 2022
INVENTOR(S) : Anthony Richard Gerardi It is certified that error appears in the above-identified patent and that said Letters Patent is hereby corrected as shown below:

On the Title Page

In item (56), in Column 2, under "Other Publications", Line 5, delete "Archieves" and insert
-- Archives --.

Signed and Sealed this
Twenty-eighth Day of January, 2025

Coke Morgan Stewart
*Acting Director of the United States Patent and Trademark Office*